United States Patent [19]

Roman

[11] 4,223,155
[45] Sep. 16, 1980

[54] 3-(HYDROCARBYLTHIOMETHYL)-2,2-DIMETHYL-CYCLOPROPANECARBOXYLATE PESTICIDES AND THEIR PREPARATION

[75] Inventor: Steven A. Roman, Oakdale, Calif.

[73] Assignee: Shell Oil Company, Houston, Tex.

[21] Appl. No.: 61,141

[22] Filed: Jul. 26, 1979

Related U.S. Application Data

[62] Division of Ser. No. 18,479, Mar. 8, 1979.

[51] Int. Cl.$^2$ ............... C07C 149/40; C07C 149/26; A01N 9/12
[52] U.S. Cl. .................. 560/15; 260/326 S; 260/347.2; 260/465 D; 260/544 S; 260/544 L; 560/17; 560/118; 560/124; 562/427; 562/431; 562/432; 562/500; 562/506; 424/274; 424/304; 424/305; 424/308
[58] Field of Search ............... 560/15, 17, 118, 124; 562/431, 432, 500, 506, 427

[56] References Cited

PUBLICATIONS

Bulletin of The World Health Organization, 44, 314–324, 1970.

*Primary Examiner*—Robert Gerstl

[57] ABSTRACT

Compounds of the formula

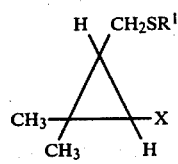

wherein $R^1$ is an optionally halo-substituted hydrocarbyl group, and X is —C(O)Cl, —C(O)Br or C(O)OR in which R is H, a salt-forming cation, an alkyl group or the residue of a pyrethroid alcohol are new pesticides or intermediates therefore. The compounds are prepared using a multi-step synthesis starting from the neutral terpene, 3-carene.

9 Claims, No Drawings

3-(HYDROCARBYLTHIOMETHYL)-2,2-DIMETHYL-CYCLOPROPANECARBOXYLATE PESTICIDES AND THEIR PREPARATION

This is a division of application Ser. No. 18,479 filed Mar. 8, 1979.

Field of the Invention

The present invention is directed to new cyclopropanecarboxylate pesticides, their use in pest control, to pest control formulations containing the new cyclopropanecarboxylates, to processes for preparation of these cyclopropanecarboxylates and to novel intermediates.

SUMMARY OF THE INVENTION

The present invention relates to new cyclopropane compounds of the formula

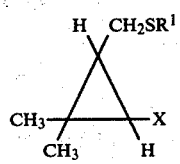

wherein $R^1$ represents an alkyl group containing from 1 to 10 carbon atoms optionally substituted by one or more halogen atoms; a (cycloalkyl)alkyl group containing from 3 to 7 ring carbon atoms, a total of from 4 to 9 carbon atoms and optionally ring-substituted by one or more halogen atoms; a cycloalkyl group containing from 4 to 7 ring carbon atoms; an alkenyl group containing from 3 to 4 carbon atoms optionally substituted by one or more halogen atoms; an alkynyl group containing from 3 to 4 carbon atoms or an aryl group containing from 6 to 12 carbon atoms or an aralkyl group containing from 7 to 10 carbon atoms, each optionally ring-substituted by one or more halogen atoms;

X is —C(O)Cl, —C(O)Br, or —C(O)OR in which R represents a hydrogen atom, a salt-forming cation, an alkyl group containing from 1 to 20 carbon atoms or a group of the formula

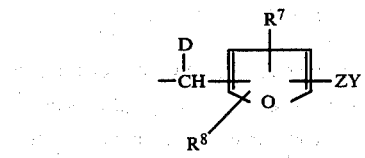 I or

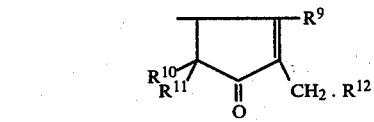 II or

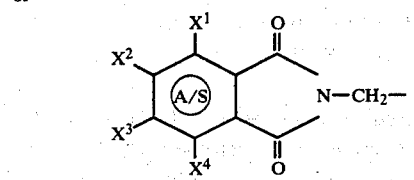 III or

-continued

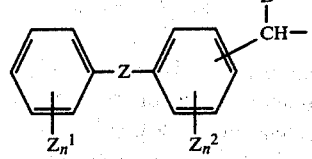 IV or

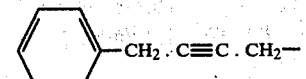 V or

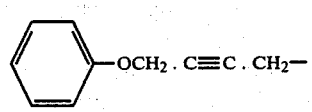 VI or

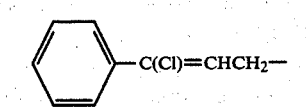 VII wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represents hydrogen or an alkyl or alkenyl group. $R^9$ represents hydrogen or a methyl group, $R^{10}$ and $R^{11}$ represent hydrogen or an alkyl group, $R^{12}$ represents an organic radical having carbon-carbon unsaturation in a position α to the $CH_2$ group to which $R^{12}$ is attached, A/S indicates an aromatic ring or a dihydro or tetrahydro analog thereof, $X^1$, $X^2$, $X^3$ and $X^4$, which may be the same or different, each represent hydrogen, halogen or a methyl group, D represents H, —CN, —C≡CH or

in which $R^{13}$ and $R^{14}$ may be the same or different, each represent a hydrogen atom or an alkyl group containing from 1 to 10 carbon atoms, Z represents —$CH_2$—, —O—, —CO—, or —S—, $Z^1$ and $Z^2$, which may be the same or different, each represent halogen or an alkyl group containing 1 to 4 carbon atoms and n is 0, 1 or 2, with the proviso that when D is —CN, —C≡CH or

then the alcohol moiety is in the R,S-racemic or in the S-optical configuration.

Representative Examples of species within the scope of the invention include:
3-phenoxybenzyl (1R,trans)-3-((cyclobutylmethylthio)methyl)-2,2-dimethylcyclopropanecarboxylate,
α-ethynyl-3-benzylbenzyl (1R,cis)-3-((1-cyclopropylmethylthiomethyl)-2,2-dimethylcyclopropanecarboxylate,
3-phenoxybenzyl (±)-(cis-trans)-3-((isobutylthio)methyl)-2,2-dimethylcyclopropanecarboxylate,
3,4,5,6-tetrahydrophthalimidomethyl (1R,cis)-3-((tert-butylthio)methyl)-2,2-dimethylcyclopropanecarboxylate, α-thioamido-3-benzylthiobenzyl (1R,cis)-3-((cyclopentylthio)methyl)-2,2-dimethylcyclopropanecarboxylate, α-cyano-3-phenoxybenzyl (1R,cis)-3-((propargylthio)methyl)-2,2-dimethylcyclopropanecarboxylate, α-cyano-3-phenoxybenzyl (1R,cis)-3-((cyclopentylthio)methyl)-2,2-dimethylcyclopropanecarboxylate, α-cyano-3-phenoxybenzyl (1R,cis)-3-((1-methylcyclopropylmethylthio)methyl)-2,2-dimethylcyclopropanecarboxylate, α-cyano-3-phenoxybenzyl (1R,cis)-3-((2-furylmethylthio)methyl)-2,2-dimethylcyclopropanecarboxylate, and α-cyano-3-phenoxybenzyl (1R,cis)-3-((2-thienylmethylthio)methyl)-2,2-dimethylcyclopropanecarboxylate.

The above esters of the present invention wherein X is C(O)OR in which R is a group of formula, I, II, III, IV, V, VI or VII are useful pest control agents.

The other cyclopropane compounds described above are useful intermediates for the production of the pest control esters.

A preferred subclass of compounds of the invention are those wherein $R^1$ is an alkyl group containing from 1 to 6 carbon atoms; a (cycloalkyl)alkyl group containing from 3 to 6 ring carbon atoms and 4 to 8 carbon atoms in the group; a cycloalkyl group containing from 4 to 6 carbon atoms; an alkenyl or alkynyl group containing from 3 to 4 carbon atoms; an aryl group containing from 6 to 12 carbon atoms or an aralkyl group containing from 7 to 10 carbon atoms and X is —C(O)OR in which R is phenoxybenzyl or especially α-cyano-3-phenoxybenzyl. The compounds wherein $R^1$ is an alkyl of from 1 to 3 carbon atoms, especially ethyl, have been found to have insecticidal activity, e.g., against corn earworm larvae.

The cyclopropane compounds exhibit optical isomerism by virtue of two asymmetric centers in the cyclopropane ring and consequently can be prepared in optically active forms, which can subsequently be mixed together, or as racemic mixtures, which can subsequently be prepared as optically active forms. Because they usually provide the highest degree of pest control, the (1R,cis) esters are preferred although the (1R,trans) esters are also active. In the esters of α-substituted alcohols in which D in formulas I or IV is other than hydrogen, there is a further possibility of optical isomerism, i.e., as R or as S optical configuration. The esters in which these alcohols exist in the R optical configuration are without practical pest control activity.

The invention also relates to processes for preparing the new pest control cyclopropanecarboxylates described above from 3-carene. When (+)-Δ³-carene is used, the pesticidal ester products can have the (1R,cis) optional configuration.

Basically, the hydrocarbylthiomethyl-2,2-dimethylcyclopropanecarboxylic acids are prepared by a multi-step process in which 3-carene having the formula VIII

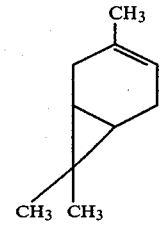

is ozonized and treated with dimethyl sulfide in methanol to form 1-(2,2-dimethoxyethyl)-2,2-dimethyl-3-(2-oxopropyl)cyclopropane, a novel chemical having the formula IX,

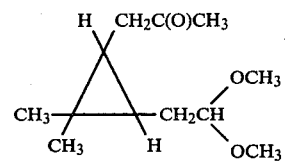

which is oxidized to (2-(2,2-dimethoxyethyl)-3,3-dimethylcyclopropyl)methyl acetate having the formula X

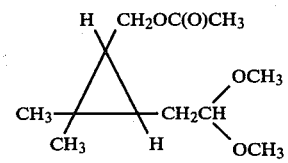

This acetate derivative is hydrolyzed in the presence of acid to (2,2-dimethyl-3-(2-oxoethyl)cyclopropyl)methyl acetate having the formula XI

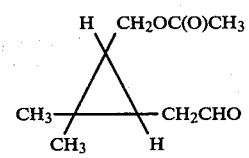

Treatment of the above compound with acetic anhydride in the presence of a base produces 2-(3-acetoxymethyl-2,2-dimethylcyclopropyl)vinyl acetate having the formula XII

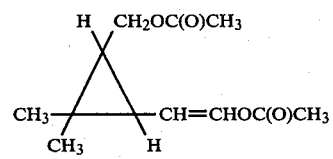

Ozonolysis and treatment with zinc of the above vinyl acetate derivative yields 3-acetoxymethyl-2,2-dimethylcyclopropanecarboxaldehyde having the formula XIII

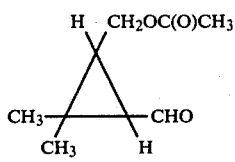

XIII

Oxidation of the above compound yields 3-acetoxymethyl-2,2-dimethylcyclopropanecarboxylic acid, having the formula XIV

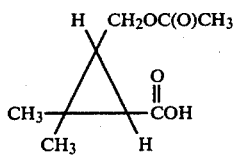

XIV

Hydrolysis of the acetate function in the presence of an inorganic base, e.g., potassium hydroxide, yields a salt of 3-hydroxymethyl-2,2-dimethylcyclopropanecarboxylate having the formula XV

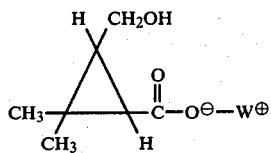

XV wherein W⊕ is a salt-forming cation obtained from the inorganic base. Treatment of the above salt with thionyl chloride produces a lactone of the formula XVI

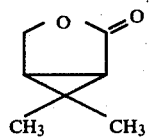

XVI which is known in *Tetrahedron Letters* No. 43, p. 3915 (1976) in the optically inactive form. This lactone is readily converted with a sulfurizing agent, such as potassium thioacetate, to the corresponding thiolactone having the formula XVII

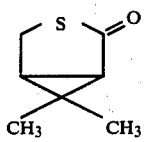

XVII

Ring opening with an inorganic base, e.g., sodium methoxide, in the presence of an alcohol ROH yields the intermediate salt having the formula XVIII

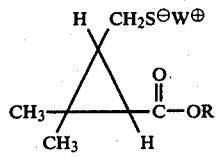

XVIII wherein W⊕ is a salt-forming cation obtained from the inorganic base and R is an alkyl group containing from 1 to 20 carbon atoms. Treatment of this salt intermediate, usually without recovering the salt from the reaction, mixture with a hydrocarbyl halide produces the 3-hydrocarbylthiomethyl-2,2-dimethylcyclopropanecarboxylate alkyl ester of formula XIX

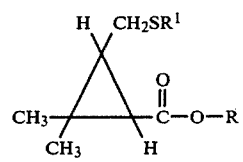

XIX

This alkyl ester is hydrolyzed to the free acid of the formula XX

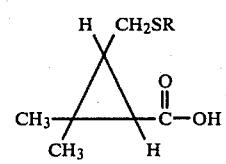

XX which acid is useful for the preparation of ester pest control agents of the invention wherein X is —C(O)OR in which R is a group of the formulas I–VII, inclusive.

The process of preparing 3-acetoxymethyl-2,2-dimethylcyclopropanecarboxylic acid is disclosed and claimed in applicant's copending U.S. Ser. No. 953,987.

The ozonolysis reactions are conducted with a gaseous mixture comprising ozone and oxygen or ozone and air. The mixture of ozone and oxygen is suitably diluted with an inert gas, such as nitrogen or argon. The ozonolysis is carried out at a temperature from about −80° C. to +20° C., preferably from about −20° C. to +20° C. It is useful in certain cases to use a solvent. Suitable solvents include aromatic hydrocarbons such as benzene and toluene, halogenated hydrocarbons, such as methylene dichloride, chloroform, and the like, lower aliphatic carboxylic acids and esters thereof such as glacial acetic acid, ethyl acetate, and the like, aliphatic hydrocarbons such as n-hexane and the like, and lower alkanols such as methanol.

Oxidation of the compound of formulas IX and XIII is conducted using reagents which convert a ketone into an ester or an aldehyde into an acid as required. For example, the compound of formula IX is oxidized by hydrogen peroxide, or a peracid, such as m-chloroperbenzoic acid, perbenzoic acid, perphthalic acid, and the like, in a suitable solvent such as chlorinated hydrocarbon, e.g., chloroform or dichloroethylene, or an ether, e.g., diethyl ether, and the compound of formula XIII is oxidized using potassium permanganate, chromic acid, potassium dichromate or the like. Such oxidations are conveniently carried out in the liquid phase by agitating, e.g., stirring a mixture of the reactants, preferably in a solvent such as an acetone-water mixture. The reaction is conducted at a temperature of from about 0° C. to about 60° C. at normal pressures. Preferably, the reactions are conducted at a temperature of from about 10° C. to about 40° C.

The thio group of derivative of formula XVIII is converted into a thio ether group by treatment with an optionally substituted hydrocarbyl halide R¹Hal in which R¹ is a group as previously defined and Hal is chlorine, bromine or iodine.

The acetal X is converted into the aldehyde of formula XI by treatment with an acidic material in an aqueous environment. Preferred acidic materials are acetic acid or hydrochloric acid used in the form of an aqueous solution thereof.

The compound of formula XI is converted into an ester derivative of formula XII by treatment with the appropriate carboxylic acid anhydride, e.g., acetic anhydride, in the presence of a basic material. Suitable basic materials include tertiary amines and alkali acetates. Preferred amines are pyridine and especially triethylamine.

The acetate derivative of formula XII is converted to the aldehyde of formula XIII by ozonolysis as previously described and by treatment with zinc in the presence of acetic acid or with a basic material, preferably triethylamine, usually in an inert solvent, such as methylene chloride or the like.

The alcohols from which the groups of formulas I through VII, inclusive, are known in the art, as for example in Elliott et al. U.S. Pat. No. 3,922,269 or Belgian Pat. No. 839,360. The pest control esters of the present invention can be prepared by esterification involving the reaction of an alcohol or derivative thereof of formula RQ, e.g., of formula IV, and a cyclopropanecarboxylic acid or derivative of formula XIX

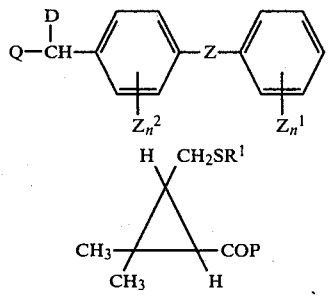

wherein Q and COP are functional groups or atoms which will react to form an ester linkage and $R^1$, D, Z, $Z^1$ and $Z^2$ are as defined above.

It is usually convenient in practice either to treat the acid or acid halide with the alcohol (COP=COOH or CO-halide and Q=OH) or to treat a halogeno compound (Q=halogen) with a salt of the carboxylic acid (COP=COO-M) where M is, for example, a silver or ammonium cation.

It can be useful to prepare the intermediate alkyl ester as tert-butyl ester (R=tert-butyl), which can be selectively converted under acid conditions as mentioned earlier to give the free acid which can be esterified, e.g., after conversion to the acid halide, to a pesticidal ester.

Suitable routes to the esters in which D is

are similar to those described in Belgian Pat. No. 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent, such as dimethylformamide or hexamethylphosphoramide. The catalyst is preferably a strong nitrogeneous base, particularly a tertiary amine such as triethylamine, trimethylamine, or the like, or an alkanolamine, such as triethanolamine, and the like. The reaction can be carried out at room temperature. It is desirable that the reaction solution be saturated with hydrogen sulfide.

Alcohols of formula RQ where R is a group of formula IV may be prepared by reduction of the corresponding acids, esters or aldehydes e.g., with hydride, or by conversion of the corresponding halide to an ester, e.g., by reaction with sodium acetate, followed by hydrolysis of the ester, or by reaction with formaldehyde of a Grignard reagent derived from an appropriate halide. The halides of formula RQ where R is a group of formula IV minus D can be prepared by halomethylation of the compound

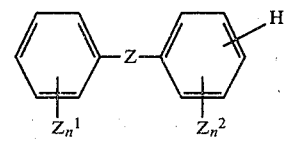

or side chain halogenation of

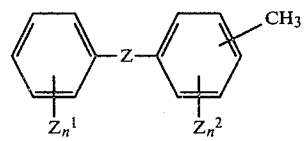

As stated earlier, the esters wherein $R^1$ is an acetyl or optionally substituted hydrocarbyl group are useful pest control agents having the ability to knockdown insects, such as houseflies, or repel mites and/or to kill insects or mites. The particular mode of pest control activity (high knockdown, repelling or killing action) can vary with the individual cyclopropanecarboxylate ester of the invention and thus depends on the specific combination of acid and alcohol moieties. In general, the pest control mode of action of the esters of the invention wherein $R^1$ is acetyl is knockdown or mite repelling rather than a killing action. In the esters wherein $R^1$ is optionally substituted hydrocarbyl, high knockdown is present and often mite repelling, insecticidal and acaricidal activity as well.

The invention includes, within its scope, pest control compositions comprising an agriculturally acceptable adjuvant—that is, at least one carrier or a surface-active agent—and, as active ingredient, at least one pest control ester of this invention. Likewise, the invention includes also a method of controlling insect, acarine or other arthropod pests at a locus which comprises applying to the pests or to the locus a pest controlling effective amount of at least one ester of the invention.

With respect to the spectrum of pesticidal activity, the compounds of this invention exhibit a selective or non-selective activity as insecticides or acaricides against one or more species of such orders as Coleoptera, Lepidoptera (especially larvae), Diptera, Orthoptera, Hemiptera, Homoptera and Acarina depending upon the specific combination of acid and alcohol moieties according to the present invention. The compositions according to the present invention are useful for controlling one or more disease carrying insects such as mosquitos, flies and cockroaches, grain insects such as rice weevil (*Sitophilus oryzae*) and mites as well as agricultural noxious insects such as planthoppers, green rice leafhopper, (*Nephotettix bipuntatus cinticeps* Uhler), diamond-back moths (*Plutella maculipennis* Curtis), imported cabbage worm (*Pieris rapae* Linne), rice stem borers (*Chilo suppressalis* Walker), corn earworm larve (*Heliothis zea* Boddie), aphids, tortrixes, leaf-miners and the like.

The pesticidal esters of the invention are used for harvested crops, horticultural application, forests, cultures in green house, and packaging materials for foodstuffs, household applications and as ectoparasiticides.

The term "carrier" as used herein means a material that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mono-, di-, and trialkyl-amines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by extrusion of plastics, agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, nonsedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboximide, octachlorodipropyl ether, isobornyl thiocyanoacetate, and other synergists used for allethrin and pyrethrin. Useful compositions can be prepared with other biological chemicals including other cyclopropanecarboxylates, organic phosphate type insecticides and carbamate type insecticides.

The compositions of the invention are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of active ingredient of this invention at the locus to be protected—i.e., the applied dosage—is of the order or 0.01% to 0.5% based on the total weight of the formulation, though under some circumstances the effective concentration will be as little as 0.001% or as much as 2%, on the same basis.

Illustrative Embodiments

The invention is illustrated by the following embodiments which describe the preparation of typical species of the invention. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT 1

(1R,cis)-1-(2,2-Dimethoxyethyl)-2,2-dimethyl-3-(2-oxopropyl)cyclopropane

Ozone was passed through 81.6 g of (+)-$\Delta^3$-carene in 140 ml of methanol at $-70°$ C. at a rate of 3 l/min for about 6 hours until appearance of a blue color indicated an excess of ozone was present in the reaction mixture. The reaction mixture was purged with air to remove excess ozone and 60 ml of methyl sulfide was added. The resulting mixture was stirred and slowly warmed to room temperature overnight, at which time the reaction mixture gas a negative test to starch-iodide paper. The methanol was stripped off and the residue was diluted with 1 liter of ether. The resulting solution was washed three times with 300 ml of water and then with 300 ml of a saturated sodium chloride solution. The organic phase was dried with magnesium sulfate, filtered and stripped to give 112.5 g of product as an oil, bp 98°–100° C. at 1 mm.

EMBODIMENT 2

((1S,cis)-(2-(2,2-Dimethoxyethyl)-3,3-dimethylcyclopropyl))methyl acetate

To a stirred solution of the product from Embodiment 1 above in 1 liter of methylene chloride at 20° C., was added 140 g of 70% m-chloroperbenzoic acid at 20°–30° C. over a period of 2 hours. The mixture was stirred at room temperature for an additional 18 hours, after which the excess peroxy acid was decomposed with 10% sodium sulfite solution. The solid products were filtered and washed with methylene chloride. The combined methylene chloride phases were washed twice with 30 ml of saturated sodium bicarbonate solution and then with saturated sodium chloride solution, dried with magnesium sulfate, filtered and stripped to give 125 g of an oil containing a small amount of solid material. This product was diluted with pentane and cooled in ice water. The resulting solid material was filtered and the remaining solution was stripped to give 112.3 g of product as an oil, bp 98°–100° C. at 1 mm.

EMBODIMENT 3

((1S,cis)-(2,2-dimethyl-3-(2-oxoethyl)cyclopropyl))methyl acetate 112 g of the product of Embodiment 2 above was treated with 1670 ml of a 2:1 solution of acetic acid: water at room temperature for 15 hours. The reaction mixture was poured into 2 liters of water and extracted two 0.5 liter portions of methylene chloride. The methylene chloride phase was washed with 2 liters of water and then with 500 ml of saturated sodium bicarbonate solution, dried with magnesium sulfate and stripped to give 85 g of product as an oil, bp 75°–77° C. at 0.4 mm.

EMBODIMENT 4

((1R,cis)-2-(3-acetoxymethyl-2,2-dimethylcyclopropyl))vinyl acetate 85 g of the product from Embodiment 3 above was treated while stirring with 99 g of triethylamine and 230 ml of acetic anhydride at room temperature for about 18 hours. The reaction mixture was diluted with ether. The resulting solution was washed with ice water, then with ice cold sodium bicarbonate solution and finally with saturated sodium chloride solution. The ether phase was dried with magnesium sulfate and stripped to give 350 g of an oil. This oil was distilled to remove acetic anhydride at 40° C. and 10 mm Hg and the resulting residue was distilled to give 80 g of product; bp 93°–96° C. at 0.1 mm Hg.

EMBODIMENT 5

(1R,cis)-3-(acetoxymethyl)-2,2-dimethylcyclopropanecarboxaldehyde

Ozone was passed through 25 g of the product from Embodiment 4 above in 150 ml methylene chloride at a rate of 3 l/min until appearance of a blue color indicated an excess of ozone was present in the reaction mixture. Ozone treatment was continued at a rate of 1 l/min for an additional 40 minutes. The reaction mixture was purged with air to remove excess ozone and stripped below 25° to a clear pale yellow oil. This oil was dissolved in 250 ml acetic acid and 40 g of zinc dust was added portionwise over a 2 hour period at 10°–20° C. The resulting mixture was stirred 2 additional hours and then filtered through celite. The filtrate was washed with water, then with saturated sodium bicarbonate solution and finally with a saturated sodium chloride solution. The resulting solution was dried with magnesium sulfate and stripped to give 16.1 g of product as a colorless oi, bp 58°–60° C. at 0.1 mm.

EMBODIMENT 6

(1R,cis)-2,2-Dimethyl-3-(acetoxymethyl)cyclopropanecarboxylic acid

To a solution of 21.0 g of the product of Embodiment 5 above, 250 ml of acetone and 50 ml of water at 5° C., was added 14.8 g of potassium permaganate portionwise over 40 minutes at 5°–10° C. The reaction mixture was then warmed to room temperature while stirring for 6 hours. The mixture was filtered and the filtrate was treated with 10% sodium bisulfite solution to destroy excess permanganate and, after filtration, stripped to remove acetone and adjusted to a pH of 4 with concentrated hydrochloric acid. The resulting solution was extracted three times with 100 ml methylene chloride. The combined methylene chloride extracts were washed with water, then with saturated sodium chloride solution, dried with magnesium sulfate and stripped to give 19 g of a thick oil which crystallized upon cooling overnight. This product was triturated with cold pentane and filtered to give 13.7 g of product as a solid; mp 78°–79° C.

EMBODIMENT 7

(1R,cis)-6,6-dimethyl-3-oxabicyclo[3.1.0]hexane-2-one

A solution of 1 g of the product of Embodiment 6 above, 0.72 g of 85% potassium hydroxide, 2.5 ml of water and 12.5 ml of methanol was stirred for two days. The reaction mixture was stripped to remove methanol and water. After the addition of 5 ml of methylene chloride, the reaction mixture was cooled and 1 ml of thionyl chloride was added. The reaction mixture was stirred until no more gas evolved. The product was filtered through celite and stripped to yield 0.6 g of a yellow oil containing some white solids. NMR and IR analyses were consistent for the desired product.

EMBODIMENT 8

(1R,cis)-6,6-dimethyl-3-thiabicyclo[3.1.0]hexane-2-one 9.2 g of the product made according to Embodiment 7 above was mixed with 21 ml of dimethylacetamide. 8.3 g of potassium thioacetate was added. The reaction mixture was immersed in an oil bath and stirred for ½ hour at 149°–152° C. The mixture was quenched in water and extracted extracted 3 times with 250 ml of pentane. The combined extracts were washed twice with 100 ml of water, dried (sodium sulfate) and stripped to give 7.6 g of product as a brown oil.

EMBODIMENT 9

Methyl (1R,cis)-3-((methylthio)methyl)-2,2-dimethylcyclopropanecarboxylate

To a cooled solution of 0.23 g of sodium in 20 ml of methanol, 1.4 g of the product of Embodiment 8 above in 5 ml of methanol was added dropwise. After stirring for 15 minutes, 0.61 ml of methyl iodide was added dropwise with cooling. After 10 minutes, the reaction mixture was quenched with water and extracted three times with 40 ml of ether. The extract was washed with water, dried with magnesium sulfate, and stripped to give 1.5 g of a yellow oil, $[\alpha]_D^{25}-6.47°$ (CHCl$_3$); c=0.02 g/cc.

EMBODIMENTS 10 THROUGH 14

Using procedures similar to those of Embodiment 9 above, the following cyclopropanecarboxylates were prepared:
methyl (1R,cis)-3-((isobutylthio)methyl)-2,2-dimethylcyclopropanecarboxylate $[\alpha]_D^{25}-13.3°$ (CHCl$_3$); c=0.02 g/cc,
methyl (1R,cis)-3-((cyclopropylmethylthio)methyl)-2,2-dimethylcyclopropanecarboxylate $[\alpha]_D^{25}-15.8°$ (CHCl$_3$); c=0.02 g/cc,
methyl (1R,cis)-3-((isopropylthio)methyl)-2,2-dimethylcyclopropanecarboxylate $[\alpha]_D^{25}-20.8°$ (CHCl$_3$); c=0.02 g/cc,
methyl (1R,cis)-3-((benzylthio)methyl)-2,2-dimethylcyclopropanecarboxylate $[\alpha]_D^{25}-5.0°$ (CHCl$_3$); c=0.02 g/cc, and
methyl (1R,cis)-3-((allylthio)methyl)-2,2-dimethylcyclopropanecarboxylate $[\alpha]_D^{25}-6.9°$ (CHCl$_3$); c=0.02 g/cc.

EMBODIMENT 15

(1R,cis)-3-((methylthio)methyl)-2,2-dimethylcyclopropanecarboxylic acid 1.2 g of the ester product of Embodiment 9 above was added to a solution of 5 ml 10% sodium hydroxide and 15 ml of methanol. The reaction was stirred at room temperature for 3 hours and refluxed for 5 hours. The resulting mixture was quenched with water, acidified and extracted with methylene chloride. The extract was dried and magnesium sulfate, filtered and stripped to yield 1.0 g of light yellow oil product, $[\alpha]_D^{25}-40.5°$ (CHCl$_3$); c=0.02 g/cc.

EMBODIMENTS 16 THROUGH 20

Using procedures similar to those of Embodiment 15 above the following cyclopropanecarboxylic acids were prepared:
3-((-isobutylthio)methyl)-2,2-dimethylcyclopropanecarboxylic acid $[\alpha]_D^{25}-36.3°$ (CHCl$_3$); c=0.02 g/cc,
3-((cyclopropylmethylthio)methyl)-2,2-dimethylcyclopropanecarboxylic acid $[\alpha]_D^{25}-40.6°$ (CHCl$_3$); c=0.02 g/cc, 3-((-isopropylthio)methyl)-2,2-dimethylcyclopropanecarboxylic acid $[\alpha]_D^{25}-46.0°$ (CHCl$_3$); c=0.02 g/cc,
3-((benzylthio)methyl)-2,2-dimethylcyclopropanecarboxylic acid $[\alpha]_D^{25}-29.0°$ (CHCl$_3$); c=0.02 g/cc, and
3-((-allylthio)methyl-2,2-dimethylcyclopropanecarboxylic acid $[\alpha]_D^{25}-27.8°$ (CHCl$_3$); c=0.02 g/cc.

EMOBDIMENT 21

α-cyano-3-phenoxybenzyl (1R,cis)-3-((methylthio)methyl)-2,2-dimethylcyclopropanecarboxylate To a solution of 0.05 g of tetrabutylammonium hydrogen sulfate, 0.05 g of benzyltriethylammonium chloride and 0.35 g of potassium carbonate in 6 ml water, was added 0.9 g of the acid product of Embodiment 15 above as a solution in 10 ml toluene. After stirring the mixture for 1 minute, 1.4 g of the α-cyano-3-phenoxybenzyl bromide was added. The resulting reaction mixture was stirred at 60°–75° C. overnight. The next day 0.05 g tetrabutylammonium hydrogen sulfate, 0.05 g benzyltriethylammonium chloride and 0.5 g potassium carbonate were added and the reaction stirred for 24 hours at 60°–70° C. The toluene layer was separated, washed successively with water, saturated sodium bicarbonate solution, and saturated sodium chloride solution, diluted with ether, dried with magnesium sulfate, filtered and stripped to yield 2.4 g of a yellow oil. The oil was added to a column of silica gel and eluted with ether-pentane (1:9) to give 1.4 g of the desired product $[\alpha]_D^{25}-13.3°$ (CHCl$_3$); c=0.02 g/cc.

EMBODIMENT 22 THROUGH 26

Using procedures similar to those of Embodiment 21 above, the following cyclopropanecarboxylates were prepared:
α-cyano-3-phenoxybenzyl (1R,cis)-3-((isobutylthio)methyl)-2,2-dimethylcyclopropanecarboxylate $[\alpha]_D^{25}-17.2°$ (CHCl$_3$); c=0.02 g/cc, α-cyano-3-phenoxybenzyl (1R,cis)-3-((cyclopropylmethylthio)methyl)-2,2-dimethylcyclopropanecarboxylate $[\alpha]_D^{25} - 17.2°$ (CHCl$_3$); c=0.02 g/cc, α-cyano-3-phenoxybenzyl (1R,cis)-3-((isopropylthio)methyl)-2,2-dimethylcyclopropanecarboxylate $[\alpha]_D^{25} - 20.5°$ (CHCl$_3$); c=0.02 g/cc, α-cyano-3-phenoxybenzyl (1R,cis)-3-((benzylthio)methyl)-2,2-dimethylcyclopropanecarboxylate $[\alpha]_D^{25} - 12.5°$ (CHCl$_3$); c=0.02 g/cc, and α-cyano-3-phenoxybenzyl (1R,cis)-3-((allylthio)methyl)-2,2-dimethylcyclopropanecarboxylate $[\alpha]_D^{25} - 10.0°$ (CHCl$_3$); c=0.02 g/cc.

In a like manner, the corresponding esters with 3-phenoxybenzyl alcohol are obtained.

EMBODIMENT

Pesticidal Activity

As one example of the pesticidal activity of the compounds of the invention, the toxicity of the compounds against corn earworm larvae was determined using the following standardized test method:

Broad bean plants were sprayed with dosages of acetone solutions of each test compound diluted into water containing an emulsifier. Immediately after spraying, 5 corn earworm larvae were transferred to the plant and held for 44–46 hours, at which time the dead and moribund were counted. The tests were conducted employing several dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects. Assigning the standard pesticide an arbitrary rating of 100, the toxicities of the compounds of the invention were expressed in terms of their Toxicity Indexes, which compares the toxicity of the compounds of the invention with that of the standard pesticide. That is to say, a test compound having a Toxicity Index of 50 would be half as active while one having a Toxicity Index of 200 would be twice as active as the standard pesticide.

Results of the tests against corn earworm larvae are shown in Table 1 below:

TABLE 1

Toxicity of 3-(Hydrocarbylthiomethyl)-2,2-dimethylcyclopropanecarboxylates Against Corn Earworm Larvae Expressed in Terms of Toxicity Index

| Compound Tested | Toxicity Index |
| --- | --- |
| Embodiment 21 | 24 |
| Embodiment 22 | 24 |
| Embodiment 23 | 35 |

TABLE 1-continued

Toxicity of 3-(Hydrocarbylthiomethyl)-2,2-dimethylcyclopropanecarboxylates Against Corn Earworm Larvae Expressed in Terms of Toxicity Index

| Compound Tested | Toxicity Index |
| --- | --- |
| Embodiment 24 | 64 |
| Embodiment 25 | 27 |
| Embodiment 26 | 32 |

I claim:

1. A compound of the formula

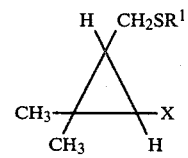

wherein R$^1$ represents an alkyl group containing from 1 to 10 carbon atoms optionally substituted by one or more halogen atoms; a (cycloalkyl) alkyl group containing from 3 to 7 ring carbon atoms, a total of from 4 to 9 carbon atoms and optionally ring-substituted by one or more halogen atoms; a cycloalkyl group containing from 4 to 7 ring carbon atoms; an alkenyl group containing from 3 to 4 carbon atoms optionally substituted by one or more halogen atoms or alkynyl group containing from 3 to 4 carbon atoms or an aryl group containing from 6 to 12 carbon atoms or an aralkyl group containing from 7 to 10 carbon atoms, each optionally ring-substituted by one or more halogen atoms; X is —C(O)OR in which R represents a hydrogen atom, a salt-forming cation, or an alkyl group containing from 1 to 20 carbon atoms.

2. A compound according to claim 1 wherein R$^1$ is an alkyl group containing from 1 to 6 carbon atoms, a (cycloalkyl)alkyl group containing from 3 to 6 ring carbon atoms and 4 to 8 carbon atoms, a cycloalkyl group containing from 3 to 6 carbon atoms, a alkenyl or alkynyl group containing from 3 to 4 carbon atoms, an aryl group containing from 6 to 12 carbon atoms or an aralkyl group containing from 7 to 10 carbon atoms.

3. A compound according to claim 2 wherein R$^1$ is an alkyl group containing from 1 to 4 carbon atoms, a cyclopropylmethyl group, an allyl group or a benzyl group.

4. A compound according to claim 4 wherein R$^1$ is allyl.

5. A compound according to claim 4 wherein R$^1$ is cyclopropylmethyl.

6. A compound according to claim 4 wherein R$^1$ is isopropyl.

7. A compound according to claim 4 wherein R$^1$ is isobutyl.

8. A compound according to claim 4 wherein R$^1$ is benzyl.

9. A compound according to claim 2 in the (1R,cis) form.

* * * * *